US010977959B2

(12) United States Patent
Byron et al.

(10) Patent No.: US 10,977,959 B2
(45) Date of Patent: Apr. 13, 2021

(54) NUTRITION GRAPH

(71) Applicant: International Business Machines Corporation, Armonk, NY (US)

(72) Inventors: Donna K. Byron, Littleton, MA (US); Michael A. Elsmore, Birmingham (GB); Sarah Maston, Portland, OR (US); David Pitera, Everett, MA (US)

(73) Assignee: International Business Machines Corporation, Armonk, NY (US)

( * ) Notice: Subject to any disclaimer, the term of this patent is extended or adjusted under 35 U.S.C. 154(b) by 250 days.

(21) Appl. No.: 15/863,788

(22) Filed: Jan. 5, 2018

(65) Prior Publication Data
US 2019/0213913 A1 Jul. 11, 2019

(51) Int. Cl.
G09B 19/00 (2006.01)
G16H 20/60 (2018.01)
G06F 16/901 (2019.01)
G06F 40/295 (2020.01)

(52) U.S. Cl.
CPC ..... G09B 19/0092 (2013.01); G06F 16/9024 (2019.01); G06F 40/295 (2020.01); G16H 20/60 (2018.01)

(58) Field of Classification Search
CPC .......... G06F 17/30345; G06F 16/9024; G06F 40/295; G09B 19/0092; G16H 20/60
See application file for complete search history.

(56) References Cited

U.S. PATENT DOCUMENTS 7,714,862 B1 * 5/2010 Dwyer .................. G06T 11/206
345/440
7,951,079 B1 5/2011 Moore
8,117,176 B2 2/2012 Lee
(Continued)

FOREIGN PATENT DOCUMENTS

TW 201445490 A 12/2017

OTHER PUBLICATIONS

Kapadia, GJ, "Cytotoxic effect of the red beetroot (*Beta vulgaris* L.) extract compared to doxorubicin (Adriamycin) in the human prostate (PC-3) and breast (MCF-7) cancer cell lines", National Institutes of Health US National Library of Medicine, https://www.ncbi.nlm.nih.gov/pubmed/21434853, Mar. 2011.
(Continued)

*Primary Examiner* — Malina D. Blaise
(74) *Attorney, Agent, or Firm* — North Shore Patents, P.C.

(57) ABSTRACT

Embodiments generally relate a nutrition graph. In some embodiments, a method includes retrieving content associated with food from one or more food data sources. The method further includes classifying the content into food and nutrients, where each food contains one or more nutrients. The method further includes retrieving content associated with health from one or more health data sources, where the content associated with health includes information on physiological characteristics. The method further includes determining one or more of the physiological characteristics associated with a person ingesting one or more of the nutrients. The method further includes mapping a particular food, one or more of the nutrients, and one or more of the physiological effects. The method further includes generating the nutrition graph based on the mapping.

18 Claims, 5 Drawing Sheets

(56) References Cited

U.S. PATENT DOCUMENTS

| | | | | |
|---|---|---|---|---|
| 8,630,448 | B1* | 1/2014 | Shanmugam | G09B 19/0092 |
| | | | | 382/100 |
| 8,690,578 | B1* | 4/2014 | Nusbaum | G09B 19/00 |
| | | | | 434/127 |
| 9,939,312 | B2* | 4/2018 | Bakhsh | A47G 21/02 |
| 10,049,598 | B1* | 8/2018 | Langheier | A61B 5/1118 |
| 10,091,972 | B1* | 10/2018 | Jensen | A01K 5/0283 |
| 2003/0059747 | A1* | 3/2003 | Yoshida | G06Q 10/10 |
| | | | | 434/127 |
| 2005/0010476 | A1* | 1/2005 | Combs | G06Q 30/02 |
| | | | | 705/2 |
| 2009/0176526 | A1* | 7/2009 | Altman | G06F 19/3475 |
| | | | | 455/556.1 |
| 2009/0275002 | A1 | 11/2009 | Hoggle | |
| 2010/0113892 | A1 | 5/2010 | Kaput et al. | |
| 2010/0216098 | A1 | 8/2010 | Montgomery | |
| 2012/0083669 | A1* | 4/2012 | Abujbara | G06F 19/3475 |
| | | | | 600/300 |
| 2012/0094258 | A1* | 4/2012 | Langheier | G16H 40/63 |
| | | | | 434/127 |
| 2012/0179665 | A1* | 7/2012 | Baarman | G06F 19/3475 |
| | | | | 707/709 |
| 2014/0172313 | A1* | 6/2014 | Rayner | G16H 50/30 |
| | | | | 702/19 |
| 2014/0315162 | A1* | 10/2014 | Ehrenkranz | G01G 19/4146 |
| | | | | 434/127 |
| 2014/0324627 | A1* | 10/2014 | Haver | G06O 30/0639 |
| | | | | 705/26.9 |
| 2015/0132722 | A1* | 5/2015 | Menczel | A61B 5/01 |
| | | | | 434/127 |
| 2015/0169758 | A1* | 6/2015 | Assom | G06F 16/36 |
| | | | | 707/603 |
| 2015/0206413 | A1* | 7/2015 | Warner | G06Q 50/22 |
| | | | | 340/573.1 |
| 2015/0269865 | A1 | 9/2015 | Volach et al. | |
| 2016/0055760 | A1 | 2/2016 | Mirabile | |
| 2016/0092653 | A1* | 3/2016 | Hendrickson | G16H 20/60 |
| | | | | 434/127 |
| 2016/0148536 | A1* | 5/2016 | Ashby | G09B 19/0092 |
| | | | | 434/127 |
| 2017/0046980 | A1* | 2/2017 | Mehta | G09B 19/0092 |
| 2017/0124912 | A1* | 5/2017 | Ashby | G09B 19/0092 |
| 2018/0233064 | A1* | 8/2018 | Dunn | G09B 19/0092 |

OTHER PUBLICATIONS

Magee, Elaine, "10 Nutrient-Rich Super Foods", WebMD Archives, http://www.webmd.com/food-recipes/10-super-foods, [retrieved Feb. 28, 2017].

Moyad, MA, "Calcium oxalate kidney stones: another reason to encourage moderate calcium intakes and other dietary changes", National Institutes of Health US National Library of Medicine, https://www.ncbi.nlm.nih.gov/pubmed/14552081, Aug. 2003.

Padayatty, Sebastian et al., "Intravenously administered vitamin C as cancer therapy: three cases", National Institutes of Health US National Library of Medicine, v. 174(7), pp. 937-942, https://www.ncbi.nlm.nih.gov/pmc/articles/PMC1405876/, Mar. 28, 2006.

United States Department of Agriculture (USDA), "USDA Database for the Flavonoid Content of Selected Foods", Release 3.1, http://www.ars.usda.gov/Services/docs.htm?docid=6231, Dec. 2013.

United States Department of Agriculture (USDA), "USDA National Nutrient Database for Standard Reference", Release 28, http://www.ars.usda.gov/Services/docs.htm?docid=8964, Sep. 2015.

* cited by examiner

NUTRITION GRAPH

BACKGROUND

Nutrition facts have been extensively researched, and research information is scattered across decades of nutrition science literature. Information such as daily-recommended nutritional values can help consumers manage their health. Consumers often rely on supplements such as multiple vitamins to ensure they ingest daily-recommended nutritional values. Yet, there is an increase in health problems and medical conditions such as obesity, high blood pressure, diabetes, and many more. Information about such nutritional values is stored in various data stores including electronic archives and databases. Information on supplements is also stored across data stores, as is research information on various health conditions. Search engines enable a user to perform searches to find such information. It is time consuming, however, and potentially overwhelming for a user to perform searches that provide pertinent information on specific health concerns, helpful pertinent nutrition information, and specific nutritional values for food that research has shown is helpful for specific health concerns. Also, some data stores are not readily accessible to the general public.

SUMMARY

Disclosed herein is a method for providing a nutrition graph, and system and computer program product as specified in the independent claims. Embodiments are given in the dependent claims. Embodiments can be freely combined with each other if they are not mutually exclusive.

Embodiments provide a nutrition graph that shows a mapping between foods, ingredients, and physiological effects. In an embodiment, a method includes retrieving content associated with food from one or more food data sources. The method further includes classifying the content into food and nutrients, where each food contains one or more nutrients. The method further includes retrieving content associated with health data from one or more health data sources, where the content associated with health includes information on physiological characteristics. The method further includes determining one or more of the physiological characteristics associated with a person ingesting one or more of the nutrients. The method further includes mapping a particular food, one or more of the nutrients, and one or more of the physiological effects. The method further includes generating the nutrition graph based on the mapping.

In another embodiment, the data sources are located in different geographic locations. In another aspect, the method further includes applying natural language processing (NLP) to the content to classify information in the content into food and nutrients. In another aspect, the method further includes determining a measurement of the amount of nutrients in particular types of food. In another aspect, the physiological characteristics include medicinal properties. In another aspect, the method further includes displaying the nutrition graph in a client device for a user to view. In another aspect, the method further includes providing the nutrition graph to an application for further processing.

DETAILED DESCRIPTION

Embodiments described herein provide nutrition graph, which facilitates healthy diet. As described in more detail herein, a system provides a nutrition graph that shows a mapping between foods, ingredients, and physiological effects. Such mappings provide a user with clear relationships between foods and medicinal powers of foods, which can help users with particular health conditions, such as weight gain, high blood pressure, diabetes, cancer, and more.

In some embodiments, a system retrieves content associated with food from one or more food data sources. The system then classifies the content into food and nutrients, where each food contains one or more nutrients. The system further retrieves content associated with health from one or more health data sources, where the content associated with health includes information on physiological characteristics. The system further determines one or more of the physiological characteristics associated with a person ingesting one or more of the nutrients. The system then maps a particular food, one or more of the nutrients, and one or more of the physiological effects. The system then generates the nutrition graph based on the mapping.

Figure 1:
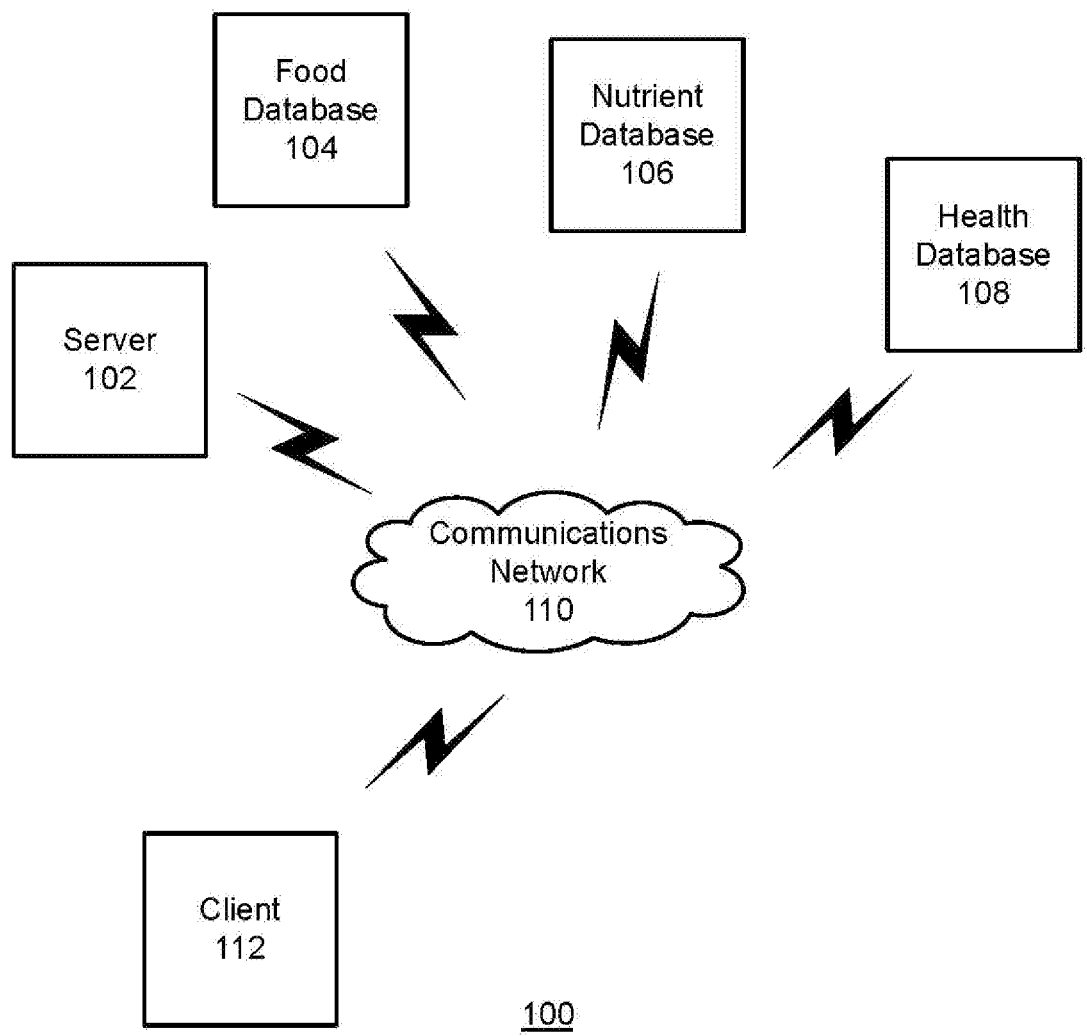
FIG. 1 is an example environment for providing a nutrition graph, according to some embodiments.

FIG. 1 is an example environment 100 for providing a nutrition graph, according to some embodiments. Shown is a server 102, a food database 104, a nutrient database 106, a health database 108, a communications network 110, and a client 112. These components of the environment 100 communicate via the communications network 110. The communications network 110 may be any network such as a wireless local area network (WLAN), Internet, etc., or combination of networks.

As described in more detail herein, the server 102 collects information associated with food, nutrients, and health conditions from the respective food database 104, the nutrient database 106, and the health database 108. In various embodiments, each database may be associated with a different entity (e.g., corporate entity, government entity, etc.). As described in more detail herein, the server 102 generates a nutrition graph from the information associated with food, nutrients, and health conditions.

As described in more detail herein, a nutrition graph shows connections between particular foods, nutrients, and health conditions. The nutrition graph is available in a central location. In various embodiments, the system provides an application programming interface (API) so that a user or organization may have a single place to access the nutrition graph.

While the server 102 performs embodiments described herein, in other embodiments, any suitable component or combination of components associated with the server 102 or any suitable processor or processors associated server 102 may facilitate performing the embodiments described herein. In various embodiments, the environment 100 may not have all of the components shown and/or may have other elements including other types of components instead of, or in addition to, those shown herein.

Figure 2:
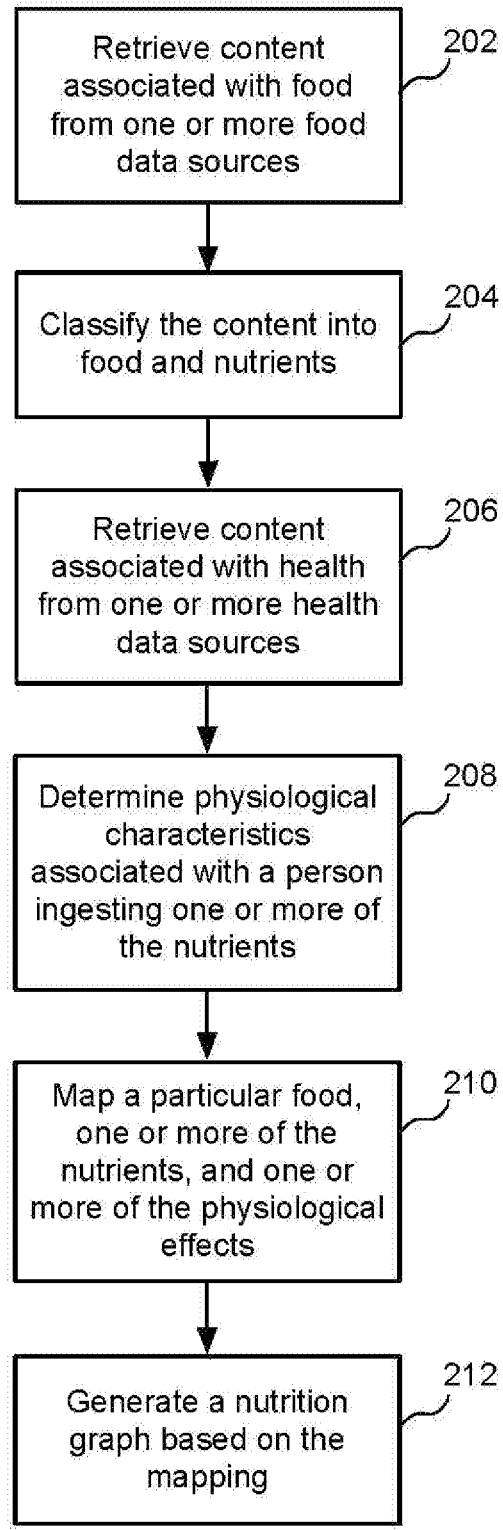
FIG. 2 is an example flow diagram for promoting healthy diet, according to some embodiments.

FIG. 2 is an example flow diagram for promoting healthy diet, according to some embodiments. As described in more detail herein, a system provides a foundational mapping and nutrition graph that shows a mapping between foods, nutrients, and physiological effects. While some embodiments are described herein in the context a single nutrition graph, these embodiments and others apply to multiple nutrition graphs. For example, the system may provide different nutrition graphs for different foods, where each nutrition graph shows a mapping between a particular food, its nutrients, and physiological effects. Referring to both FIGS. 1 and 2, a method begins at block 202, where a system such as server 102 retrieves content associated with food from one or more food data sources. As indicated herein, the server 102 collects information associated with food and nutrients from the respective food database 104 and the nutrient database 106. In some embodiments, the data sources are located in different geographic locations. In various embodiments, each database may be associated with a different entity (e.g., corporate entity, government entity, etc.). In some embodiments, the system sends a request for content to the data sources, receives the content, and stores the content in storage associated with the system. In various embodiments, the data sources are well known, standardized, and reliable, such as the United States Department of Agriculture (USDA) food database.

In block 204, where system classifies the content into food and nutrients, where each food contains one or more nutrients. In various embodiments, the system applies natural language processing (NLP) and analytic analysis to the content to classify information in the content into food and nutrients. In some implementations, the system classifies the information in the content to food, food groups, and nutrients, where each food is a member of a food group, and each food contains various nutrients. Such content may include macronutrients, micronutrients, as well as other elements such as allergens, phytochemicals, etc.

In some embodiments, the system may take a flattened relational model of seed data (e.g., USDA seed data) to break food related information into categories of food, food group, and nutrient. As described in more detail herein, the system may access electronic dictionaries to assist in classifying the content. Also, the system may classify some content based on contextual information. In some embodiments, the system determines whether a food is a member of a food group and if the food is a source of one or more nutrients. For example, the system may determine the phytonutrients of a particular food, using both public information available from the USDA and other resources that list the biological components of foods. In some embodiments, the system determines a measurement of the amount of nutrients in particular types of food. The system may determine such measurements from the content and stores the measurements.

In block 206, where a system such as server 102 retrieves content associated with health from one or more health data sources. As indicated herein, the server 102 collects information associated with health such as health conditions and illness from the health database 108. In some embodiments, the system sends a request for content to the data source, receives the content, and stores the content in storage associated with the system. In various embodiments, the data sources are well known, standardized, and reliable, such as the U.S. National Institutes of Health's National Library of Medicine (NIH/NLM), also known as "PubMed." In various embodiments, the content associated with health includes information on physiological characteristics, information on health conditions, and information on illnesses.

In block 208, where the system determines one or more of the physiological characteristics associated with a person ingesting one or more of the nutrients. In various embodiments, the system determines one or more of the physiological characteristics by applying analytic analysis to various sources of food information, nutrient information, and information on physiological characteristics. In various embodiments, the physiological characteristics are associated with food, food components, nutrients, and how such food, food components, nutrients affect the human body, including how such food, food components, and nutrients affect health conditions and illness. Health conditions 314 may include, for example, high blood pressure, weight gain, etc. Illness 316 may include, for example, diabetes, cancer, etc. For example, tomatoes have lycopene, which is known to help prevent particular diseases such as cancer.

In some embodiments, some physiological characteristics may include medicinal properties. Medicinal properties are properties having healing and/or therapeutic effects on a person. For example, a dark-colored grape contains the phytochemicals (phytonutrient nodes) anthocyanin and proanthocyanidin. These phytochemicals are not found on the nutrient label and these phytochemicals have been connected in the nutrition literature as especially good for the immune system. In another example, vitamin C is an anti-oxidant, and anti-oxidants minimize the cell damage that leads to heart disease. Such connections between food, nutrients, health conditions, and disease may enable users to prevent or reverse particular health conditions and illness. In another example, some phytonutrients help with various physiological processes that fight diseases. The nutrition graph reveals such connections.

Connections revealed by the nutrition graph may positive or negative. For example, in some embodiments, some physiological characteristics may also include harmful properties. Harmful properties are properties that increase adverse health risks. For example, ingestion of some oxalates may be correlated with kidney stones and should be avoided. As such, some foods may have components having physiological characteristics that may be harmful. As such, the system may flag some foods having harmful physiological characteristics, and the system may provide warnings in the nutrition graph of phytonutritents that may be harmful in order to avoid certain unhealthy conditions.

In block 210, where the system maps a particular food, one or more of the nutrients, and one or more of the physiological effects. In various embodiments, the system determines a specific set of food attributes that correlate to particular physiological characteristics, including genetic, biochemical, proteomic, enzymatic biomarkers to assist with nutritional personalization accuracy of health outcomes. The particular combination of food and biomarker attributes may vary. As a result, the system may determine a relationship between otherwise unconnected nutritional and physiological characteristics, including associated health conditions, diseases, and/or disorders. As indicated herein, physiological characteristics may be medicinal or harmful.

Figure 3:
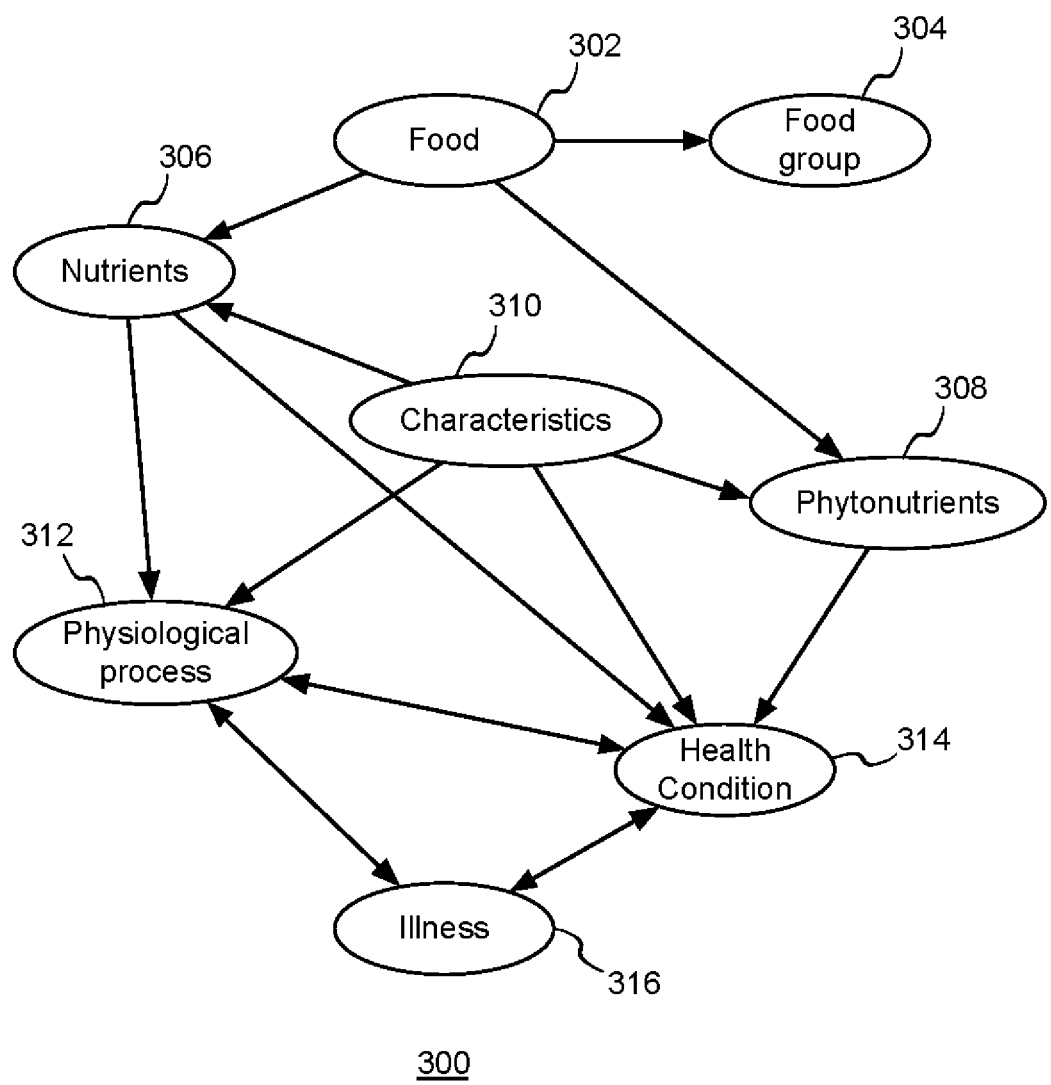
FIG. 3 is an example map of information for providing a nutrition graph, according to some embodiments.

FIG. 3 is an example map 300 of information for providing a nutrition graph, according to some embodiments. This particular example map 300 shows relationships between food and other information such as the physiology of the human body. For example, a particular food 302 may be a part of a food group 304. The food 302 may have particular nutrients 306 and phytonutrients 308. While nutrients 306 and phytonutrients 308 are shown as separate nodes, nutrients 306 may be treated as a broad category of different types of nutrients, where nutrients 306 include phytonutrients 308.

In various embodiments, nutrients 306 and phytonutrients 308 may have characteristics 310, and may be associated with physiological processes 312 and health conditions 314. Furthermore, physiological processes 312, health conditions 314, and illness 316. Health conditions 314 may include, for example, high blood pressure, weight gain, etc. Illness 316 may include, for example, diabetes, cancer, etc.

For example, phytochemicals are chemicals produced by plants that are not found on the back of USDA labels. Phytochemicals tend to have medicinal properties. In some embodiments, the system may access a food dictionary from the USDA, a nutrient dictionary from the USDA, a phytonutrient dictionary from a physical response dictionary, and a condition dictionary.

In some embodiments, the system may use non-statistical natural language processing (NLP) methods to fetch defined relationships between entities and/or add more elements to existing dictionaries. The system grows the nutrition graph over time using an NLP research engine. The system stores the various information such as food, nutrient, phytochemical, physiological, body component data (including associated health conditions and diseases) in an existing nutrition graph. These various types of information may be referred to as entities, and these entities may be referred to as nodes in the graph. The system trains the NLP engine to search for these entities in the research text of various documents.

In various embodiments, these entities (e.g., food, nutrient, phytochemical, physiological, body component data, etc.) in the research text are connected by key words. For example, information in research text may connect vitamin C to cancer prevention. The system creates connections between particular entities (e.g., a vitamin C node, a cancer node, etc.) in the nutrition graph by creating vertices (edges).

In some embodiments, the system determines the strength of a connection between two given entities or nodes. The system trains the NLP research engine to know the connection between the nutrient vitamin C and the disease cancer. The system also associates new information found on these entities with the existing information or nodes of these two entities in the nutrition graph. Accordingly, in this example, the two nodes (vitamin C and cancer) in the nutrition graph gain more edges (connections/relationships) between the two nodes over time with the addition of more found medical research supporting the connection. In other words, connections grow stronger with more evidence from research.

In some embodiments, the system may assign a score to a connection between two nodes depending on the strength of the connection. For example, a low score may be assigned to a weak connection. A weak connection between two nodes may be one where there is only one or a few references to the connection in the research text. A high score may be assigned to a strong connection, where there are many references to the connection in the research text. The connection gets stronger with more references in the text of one or more research sources or documents.

In some embodiments, the system may apply weights to a score depending on the research text. For example, referenced connections over multiple research documents may receive more weight (resulting in a higher score) than the same number of connections in the same research document. In some embodiment, referenced connections in research documents from some sources (e.g., predetermined reputable sources, etc.) may receive more weight than other sources.

In some embodiments, the system trains the NLP engine to know result thresholds, where a certain amount of a particular nutrient (above the result threshold) may have a positive impact or a negative impact on the body's physiological process. Such result thresholds may include positive result thresholds and negative result thresholds.

In some embodiments, the connections/edges between two nodes may contain information on the positive or negative impacts. The system may indicate an amount of a nutrient that would cause a significant positive impact or a significant negative impact based on whether the nutrient amount exceeds the respective positive result threshold or negative result threshold.

In some embodiments, the positive or negative result thresholds reflect ranges for various measures of nutrients, which are available in clinical dictionaries and made available to the system. For example, the recommended daily allowances for vitamins that have a positive result threshold for a given nutrient (e.g., vitamin C) have a positive impact on the body's physiological process. These threshold levels can enable the system to know if a food is "high" or "low" in a particular nutrient component. The system may train the NLP engine to determine whether a research result is "good" or "excellent" as far as helping or harming. In some embodiments, the system may determine and provide information on cooking methods for preparing particular types of food in order to meet particular positive result thresholds or to stay under particular negative result thresholds. For example, a boiled beet will have less iron than one that has been baked due to the effect of water based cooking methods on vitamin C, which carries the iron.

The system scrapes articles while looking for specific phrases, e.g., "contains . . . ," etc., or looking for specific words, e.g., "vitamin A, etc." In the non-statistical scrapings, the system searches dictionaries for mentions of the entities, and reviews grabbed sentences for connections between existing entities. The system parses phrases, and grabs new defined content items, e.g., "there is a high probability that (food) contains (nutrient)," "(food) be harmful to (biological entity)," "(food) reduced (condition)," etc.

The system may use statistical NLP methods to grab defined relationships between content items/entities, and/or add more elements to existing dictionaries. The system may also use techniques for completing such tasks such as named entity recognition, relation extraction, etc. The system may also use statistical models involving annotating a large corpus of ground truth data. Annotating a corpus involves marking certain words as certain defined entities (e.g., labeling text as food, nutrient, phytonutrient, physical response, condition, etc.), as well as linking those defined entities that share a defined connection, e.g., "food contains (nutrient)". Once the corpus is marked with examples, additional instances can be extracted from the text corpus. For example, when the marked text provided many example phrasings such as "(food) reduced (condition)," and within the research text a new sentence is detected expressing FOOD1, a word very similar to 'reduced', and CONDITIONA, the relation FOOD1 reduces CONDITIONA can be added to the graph, or proposed as an addition pending human review. In this way additional nodes in the graph are discovered by extending the set of known (food) concepts, (condition) concepts, or relation expressions (e.g. variants of 'reduced').

Referring still to FIG. 2, in block 212, where the system generates a nutrition graph based on the mapping. In various embodiments, the graph is a recording of the mapping in a graphical form. For example, the application may display the nutrition graph in a client device for a user to view.

In some implementations, the mapping of a particular food, of one or more of the associated nutrients, and of one or more of the associated physiological effects provide a map or nutrition graph. The nutrition graph breaks out the nutritional components of foods and maps how they affect different conditions and physiology.

In various embodiments, the system may store the nutrition graph in a graph database, where the graph shows the relationship between food, nutrients, phytonutrients and physiology, disease, etc. This provides a centralized place for the nutrition graph that show the relationships between various foods, nutrients, physiological characteristics, including associated health conditions, diseases, and disorders, etc. The nutrition graph can be updated with new pertinent information as needed.

Figure 4:
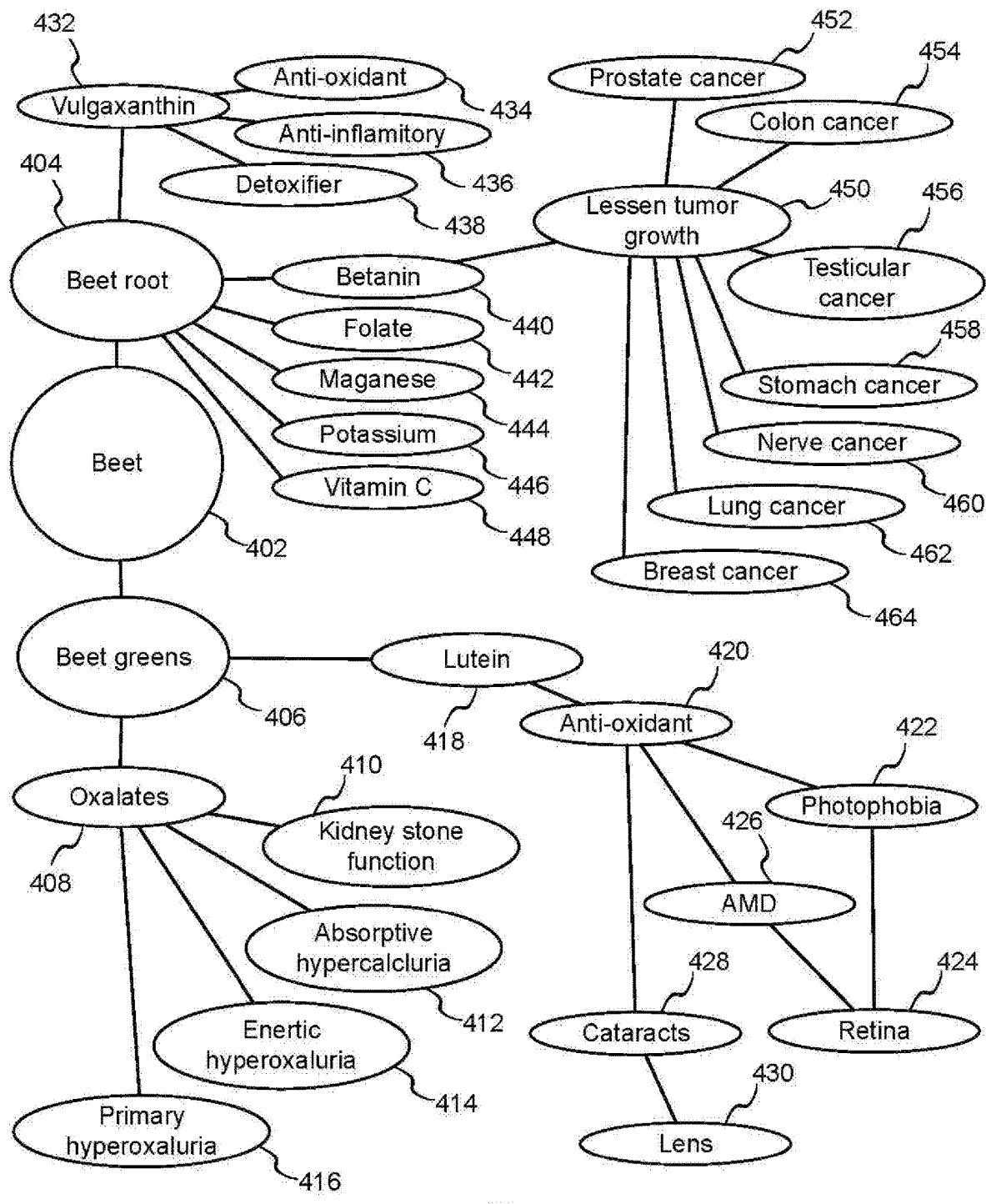
FIG. 4 is an example nutrition graph, according to some embodiments.

FIG. 4 is an example nutrition graph 400, according to some embodiments. In various scenarios, a beet 402 has components; a beet root 404 and leaves or beet greens 406. Each food component may have nutrients that have various medicinal properties. For example, the beet greens 406 has oxalates 408, which is a type of organic acid. Oxilates 408 may have various physiological effects. For example, oxilates 408 may affect kidney stone function 410, absorptive hypercalcluria 412, enertic hyperoxaluria 414, primary hyperoxaluria 416, etc. Oxilates 408 have an associated risk of kidney stones.

In some embodiments, the system may provide additional information on each node shown such as whether a particular associated physiological effect is positive (e.g., likely to cure kidney stones) or negative (e.g., likely to cause kidney stones). In some embodiments, the system may also provide additional information such as quantities of particular food components and/or nutrients have significant physiological effects.

The beet greens 406 have lutein 418, which is an anti-oxidant 420. The anti-oxidant 420 may affect photophobia 422, which affects the retina 424. The anti-oxidant 420 may also affect age-related macular degeneration (AMD) 426, which also affects the retina 424. The anti-oxidant 420 may also affect cataracts 428, which affects the eye lens 430. Accordingly, beet greens 406 have anti-oxidants that are good for the eyes.

The beet root 404 has vulgaxanthin 432, which is an anti-oxidant 434, an anti-inflamatory 436, and detoxifier 438. The beet root 404 also has betanin 440, folate 442, maganese 444, potassium 446, and vitamin C 448.

Betanin 440 has a particular medicinal property of lessening tumor growth 450 of various cancers such as prostate cancer 452, colon cancer 454, testicular cancer 456, stomach cancer 458, nerve cancer 460, lung cancer 462, and breast cancer 464. Accordingly, betanin 440 fights cancer. While the beet greens 406 may lessen tumor growth, the beet greens 406 may also introduce a risk for kidney stone issues. In some embodiments, the system indicates how much beet greens 406 may lessen tumor growth, and how much beet greens 406 introduce a risk for kidney stone issues.

As shown in the nutrition graph 400, a particular food such as beets are mapped to nutrients, which are mapped to specific functions of human anatomy, which are mapped to specific health conditions and diseases. Also, such a nutrition graph may help a person know what foods to avoid that may aggravate particular health conditions such as allergies, kidney stones, etc.

The nutrition graph provides insight into medically complex situations to a person with limited medical and nutritional training.

Although the steps, operations, or computations may be presented in a specific order, the order may be changed in particular embodiments. Other orderings of the steps are possible, depending on the particular embodiment. In some particular embodiments, multiple steps shown as sequential in this specification may be performed at the same time. Also, some embodiments may not have all of the steps shown and/or may have other steps instead of, or in addition to, those shown herein.

In some implementations, the system may provide the nutrition graph to an application for further processing. For example, a food tracker application may utilize the nutrition graph in order to help users with weight loss or manage health conditions such as blood pressure, diabetes, cataracts, kidney stones, cardio vascular disease, etc. The nutrition graph may help to provide a recommended diet to treat a condition. For example, a nutrition graph may help to track the properties of the foods (e.g., foods high in antioxidants, etc.). The system may provide an application programming interface (API) to the mapping in order to enable applications to retrieve the nutritional graph. The API may be published as a service and as a nutrition graph, which can be a resource for a variety of applications such as an online research service for nutritionist and academic communities, electronic health record (EHR) systems, personalized patient care, etc.

The nutrition graph may be used in an EHR system to make nutritional recommendations to be communicated to a patient. The nutrition graph may provide a list of foods that have dangerous interactions with a condition and that the patient should avoid, thereby improving the quality of care for the patient. In some embodiments, the nutrition graph may alert a hospital clinician of any potential risks associated with some foods that a person might ingest.

In some embodiments, the API may be available to food journal applications, recipe applications, menu-planning applications, etc., to enable such applications to be more intelligent around a specific diagnosed condition or chronic illness. Developers may design apps able to catalogue and manage recipes. Social applications may be developed for communities of people to share recipes they find.

Figure 5:
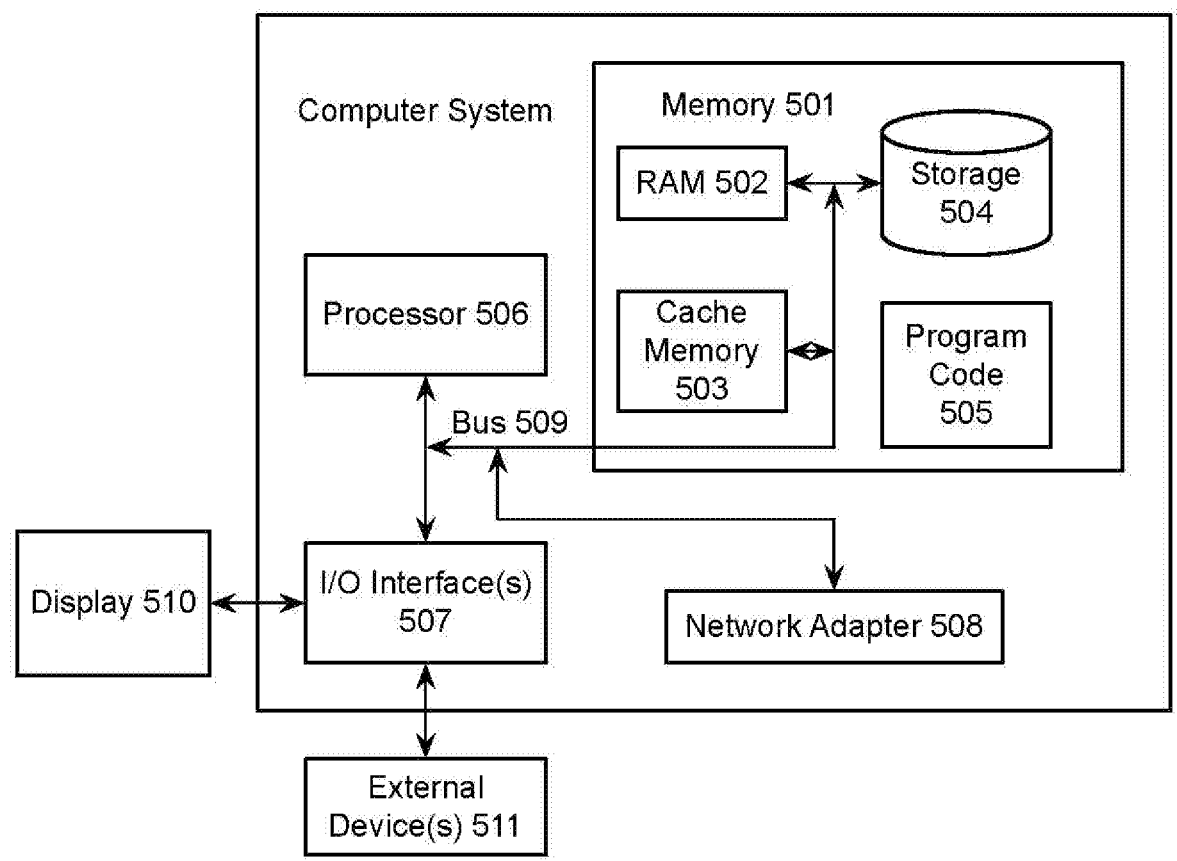
FIG. 5 is a block diagram of an example computer system, which may be used for embodiments described herein.

FIG. 5 is a block diagram of an example computer system 500, which may be used for embodiments described herein. In various embodiments, the server 102 may include a computer system such as computer system 500 according to embodiments of the present invention, as illustrated in FIG. 5. The computer system 500 is operationally coupled to one or more processing units such as processor 506, a memory 501, and a bus 509 that couples various system components, including the memory 501 to the processor 506. The bus 509 represents one or more of any of several types of bus structure, including a memory bus or memory controller, a peripheral bus, an accelerated graphics port, and a processor or local bus using any of a variety of bus architectures. The memory 501 may include computer readable media in the form of volatile memory, such as random access memory (RAM) 502 or cache memory 503, or storage 504, which may include non-volatile storage media or other types of memory. The memory 501 may include at least one program product having a set of at least one program code module 505 that are configured to carry out the functions of embodiment of the present invention when executed by the processor 506. The computer system 500 may also communicate with a display 510 or one or more other external devices 511 via I/O interfaces 507. The computer system 500 may communicate with one or more networks, such as communications network 110, via network adapter 508.

The descriptions of the various embodiments of the present invention have been presented for purposes of illustration, but are not intended to be exhaustive or limited to the embodiments disclosed. Many modifications and variations will be apparent to those of ordinary skill in the art without departing from the scope and spirit of the described embodiments. The terminology used herein was chosen to best explain the principles of the embodiments, the practical application or technical improvement over technologies found in the marketplace, or to enable others of ordinary skill in the art to understand the embodiments disclosed herein.

The present invention may be a system, a method, and/or a computer program product at any possible technical detail level of integration. The computer program product may include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may include copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, configuration data for integrated circuitry, or either source code or object code written in any combination of one or more programming languages, including an object oriented programming language such as Smalltalk, C++, or the like, and procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the blocks may occur out of the order noted in the Figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

What is claimed is:

1. A computer-implemented method for providing a nutrition graph, the method comprising:
   retrieving, by a processor, food content associated with one or more food items from one or more food databases;
   classifying, by the processor, the food content into one or more food types and one or more nutrients, wherein each food item of the one or more food items is associated with the one or more nutrients;
   retrieving, by the processor, health content associated with health from one or more health databases, wherein the health content includes information on one or more physiological characteristics;
   determining, by the processor, the one or more physiological characteristics associated with a person ingesting the one or more nutrients, wherein the one or more physiological characteristics include positive health properties and negative health properties;
   generating, by the processor, nodes for the nutrition graph, wherein the nodes represent at least one food item of the one or more food items, the one or more nutrients, and the one or more physiological characteristics;
   generating, by the processor, edges between one or more pairs of the nodes;
   computing, by the processor, strength values of the edges between the one or more pairs of the nodes;
   training, by the processor, at least one research engine based on the edges between the one or more pairs of nodes;
   generating, by the processor, the nutrition graph based on the nodes and edges and information stored in the at least one research engine; and
   displaying, by the processor, the nutrition graph on a display of a client device for a user to view.

2. The method of claim 1, wherein the one or more food databases are located in different geographic locations.

3. The method of claim 1, further comprising applying natural language processing (NLP) to the food content to classify information in the food content into the one or more food types and the one or more nutrients.

4. The method of claim 1, further comprising determining a measurement of an amount of the one or more nutrients in the one or more food types.

5. The method of claim 1, wherein the physiological characteristics include medicinal properties.

6. The method of claim 1, further comprising providing the nutrition graph to an application for further processing.

7. The method of claim 1, further comprising:
   retrieving one or more of a positive threshold value and a negative threshold value for each nutrient of the one or more nutrients; and
   computing if each nutrient of the at least one food item of the one or more food items meets the positive threshold value or the negative threshold value.

8. A computer program product for providing a nutrition graph, the computer program product including at least one computer readable storage medium having program instructions embodied therewith, the program instructions executable by at least one processor to cause the at least one processor to perform operations comprising:
   retrieving, by the at least one processor, food content associated with one or more food items from one or more food databases;
   classifying, by the at least one processor, the food content into one or more food types and one or more nutrients, wherein each food item of the one or more food items is associated with the one or more nutrients;
   retrieving, by the at least one processor, health content associated with health from one or more health databases, wherein the health content includes information on one or more physiological characteristics;
   determining, by the at least one processor, the one or more physiological characteristics associated with a person ingesting the one or more nutrients, wherein the one or more physiological characteristics include positive health properties and negative health properties;
   generating, by the processor, nodes for the nutrition graph, wherein the nodes represent at least one food item of the one or more food items, the one or more nutrients, and the one or more physiological characteristics;
   generating, by the processor, edges between one or more pairs of the nodes;
   computing, by the processor, strength values of the edges between the one or more pairs of the nodes;
   training, by the processor, at least one research engine based on the edges between the one or more pairs of nodes;
   generating, by the at least one processor, the nutrition graph based on the nodes and edges and information stored in the at least one research engine; and
   displaying, by the at least one processor, the nutrition graph on a display of a client device for a user to view.

9. The computer program product of claim 8, wherein the one or more food databases are located in different geographic locations.

10. The computer program product of claim 8, wherein the at least one processor further performs operations comprising applying natural language processing (NLP) to the food content to classify information in the food content into the one or more food types and the one or more nutrients.

11. The computer program product of claim 8, wherein the at least one processor further performs operations comprising determining a measurement of an amount of the one or more nutrients in the one or more food types.

12. The computer program product of claim 8, wherein the physiological characteristics include medicinal properties.

13. The computer program product of claim 8, wherein the at least one processor further performs operations comprising providing the nutrition graph to an application for further processing.

14. A system comprising:
   comprising at least one processor and a computer readable storage medium having program instructions embodied therewith, the program instructions executable by the first processor to cause the at least one processor to perform operations comprising:

retrieving, by the at least one processor, food content associated with one or more food items from one or more food databases;

classifying, by the at least one processor, the food content into one or more food types and one or more nutrients, wherein each food item of the one or more food items is associated with the one or more nutrients;

retrieving, by the at least one processor, health content associated with health from one or more health databases, wherein the health content includes information on one or more physiological characteristics;

determining, by the at least one processor, the one or more physiological characteristics associated with a person ingesting the one or more nutrients, wherein the one or more physiological characteristics include positive health properties and negative health properties;

generating, by the processor, nodes for the nutrition graph, wherein the nodes represent at least one food item of the one or more food items, the one or more nutrients, and the one or more physiological characteristics;

generating, by the processor, edges between one or more pairs of the nodes;

computing, by the processor, strength values of the edges between the one or more pairs of the nodes;

training, by the processor, at least one research engine based on the edges between the one or more pairs of nodes;

generating, by the at least one processor, the nutrition graph based on the nodes and edges and information stored in the at least one research engine; and displaying, by the at least one processor, the nutrition graph on a display of a client device for a user to view.

15. The system of claim 14, wherein the one or more food databases are located in different geographic locations.

16. The system of claim 15, wherein the at least one processor further performs operations comprising applying natural language processing (NLP) to the food content to classify information in the food content into the one or more food types and the one or more nutrients.

17. The system of claim 15, wherein the at least one processor further performs operations comprising determining a measurement of an amount of the one or more nutrients in the one or more food types.

18. The system of claim 15, wherein the physiological characteristics include medicinal properties.

* * * * *